United States Patent
Palmieri et al.

(10) Patent No.: US 6,342,489 B1
(45) Date of Patent: Jan. 29, 2002

(54) BILE ACID SALTS OF METALS WITH PHYSIOLOGICAL ACTION AND THE USE THEREOF IN THERAPY

(75) Inventors: Beniamino Palmieri, Via Bisi, 125 - Modena (IT), 41100; Alessandro Medici, Via Libia, 10, Bologna (IT), 40138; Enzo Bartoli, Reggio Emilia (IT)

(73) Assignees: ICE s.r.l., Reggio Emilia; Beniamino Palmieri, Modena; Alessandro Medici, Bologna, all of (IT)

( * ) Notice: Subject to any disclaimer, the term of this patent is extended or adjusted under 35 U.S.C. 154(b) by 0 days.

(21) Appl. No.: 09/509,891

(22) PCT Filed: Oct. 9, 1997

(86) PCT No.: PCT/EP97/05555

§ 371 Date: Apr. 4, 2000

§ 102(e) Date: Apr. 4, 2000

(87) PCT Pub. No.: WO99/19342

PCT Pub. Date: Apr. 22, 1999

(51) Int. Cl.[7] ............... A61K 31/56; C07J 41/00
(52) U.S. Cl. ............ 514/169; 514/171; 514/182; 552/548; 552/549; 552/550; 552/551
(58) Field of Search ............... 552/548, 549, 552/550, 551; 514/169, 171, 182

(56) References Cited

U.S. PATENT DOCUMENTS

| | | | | |
|---|---|---|---|---|
| 3,620,831 A | * | 11/1971 | Gould | 117/201 |
| 4,202,876 A | * | 5/1980 | Monks et al. | 424/1.5 |
| 5,079,240 A | * | 1/1992 | Hofmann | 514/182 |
| 5,174,897 A | * | 12/1992 | Takaichi et al. | 424/9 |
| 5,415,872 A | | 5/1995 | Sipos | 424/490 |
| 5,460,812 A | | 10/1995 | Sipos | 424/94.1 |
| 5,578,304 A | | 11/1996 | Sipos | 424/94.1 |

FOREIGN PATENT DOCUMENTS

GB 1091252 * 11/1967

OTHER PUBLICATIONS

Huang, W. D., et al "EXAFS and FTIR studies on the binding of deoxycholic acid . . . " Biospectroscopy, vol. 1, No. 4, pp. 291–296, 1995.*

Nakahara, M., et al "On the preparations of metal complexes. V." Bull. Chem. Soc. Jap., vol. 43, No. 10, pates 3150–3155, 1970.*

* cited by examiner

Primary Examiner—Paul J. Killos
Assistant Examiner—Leigh C. Maier
(74) Attorney, Agent, or Firm—Nixon & Vanderhye

(57) ABSTRACT

Bile acid metal salts of therapeutic interest and pharmaceutical and veterinary composition containing same for the treatment of anemias and other conditions are described.

6 Claims, 2 Drawing Sheets

BILE ACID SALTS OF METALS WITH PHYSIOLOGICAL ACTION AND THE USE THEREOF IN THERAPY

This application is a 35 U.S.C. § 371 of PCT/EP97/05555, filed Oct. 9, 1997.

The present invention relates to therapeutically interesting bile acid metal salts.

The invention also relates to pharmaceutical and veterinary compositions containing said salts.

A number of metal cations exist playing a physiological role: in addition to iron, which is a component of hemoglobin, varying amounts of zinc, copper, selenium, molybdenum, cobalt, manganese etc., known as oligoelements, are necessary for a correct function of the enzyme and physiological systems. These elements are usually absorbed through the diet, but pathological or alimentary deficiency conditions exist in which a pharmacological supply or the dietary supplement through the administration of suitable salts or complexes is desired.

The problem is particularly felt in the case of iron, the administration of which is often required for the treatment of iron-deficiency anemias. For this purpose, salts such as ferrous gluconate or sulfate or complexes of iron with succinylated proteins are used at present.

DESCRIPTION OF THE INVENTION

Figure 1:
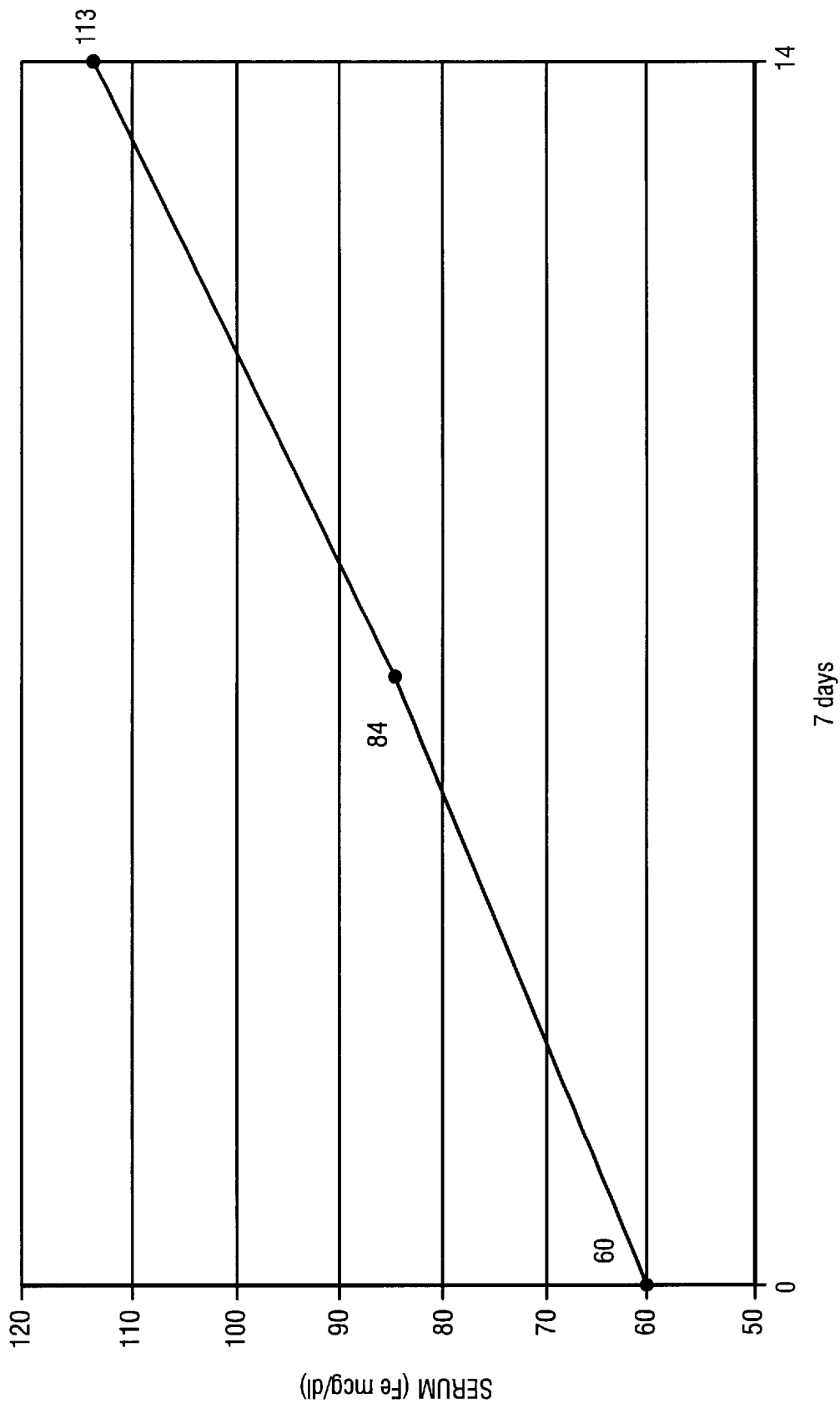
FIG. 1 is a graph of serum iron concentration (Fe mcg/dl) over a period fourteen days after administration of 19.2 mg iron per day in the form of ferric ursodeoxycholate to a first iron-deficient patient

Now it has been found that the above cited bile acid metal salts provide a high, gradual absorption of the metal cation which can selectively be carried into the entero-hepatic circle.

The use of the bile acids as carriers for iron or for oligoelements turned out to be particularly advantageous and allowed to overcome some of the drawbacks affecting the compounds of the prior art.

Bile acids, in fact, acting as intestinal barrier permeation factors, provide a higher bioavailability also thanks to their recycle effect through the entero-hepatic circle, thereby assuring a gradual absorption kinetics. Moreover, particularly in the case of the iron salts, the typical side-effects of the oral administration of these compounds, such as constipation, gastroenteral intolerance, meteorism, epigastralgias, are avoided.

The salts of the invention can be prepared according to conventional methods, reacting natural bile acids or the derivatives thereof with metal hydroxides, or by interchange reactions between suitable metal salts and bile acid alkali or alkaline-earth salts.

Examples of natural bile acids comprise cholic, deoxycholic, chenodeoxycholic, chenocholic, ursocholic, ursodeoxycholic, hyodeoxycholic acids and the corresponding tauro- and glyco- conjugates.

The natural bile acids can optionally be derivatized introducing further salifiable acid groups, for example by reaction with anhydrides of di- or poly-carboxylic acids, such as succinic, glutaric, cyclohexanedicarboxylic acids.

Some of said derivatives are known and can anyway be prepared according to conventional methods, such as those described in Italian Patent n. 1.163.090.

A different approach is the ketalization of the keto groups present in the bile acid molecule with tartaric acid, and of hyocholic acid with ketomalonic acid.

The presence of more salifiable groups per bile acid molecule provides an increase in the metal cation/bile acid molar ratio, when this is desirable for therapeutical and application purposes.

Natural or semisynthetic bile acids can be salified according to the invention with metals selected from the group consisting of iron (II), iron (III), copper (I), copper (II), zinc, cobalt, molybdenum, platinum, gold, manganese, vanadium, selenium, tin, nickel.

Particularly preferred are ferrous or ferric salts, particularly the ferric ones, which can be used for the treatment of iron deficiencies in man and animals.

For the envisaged therapeutical uses or for further uses, the salts of the invention can be formulated in pharmaceutical compositions, according to conventional techniques and excipients such as those described in Remington's Pharmaceutical Sciences Handbook, Mack. Pub., N.Y., U.S.A.

Examples of said compositions comprise capsules, tablets, syrups or drinkable solutions, gastric and/or controlled release forms and the like. The daily dosage will depend of course on the type of cation: in the case of iron, the salts of the invention can be administered in doses varying from 100 mg to 3 g, one to four times daily.

The salts of the invention can moreover be present in the composition of dietetic or alimentary formulations for the human or veterinary use, optionally in combination with other components with a complementary or anyway useful activity.

The following examples further illustrate the invention.

EXAMPLE 1

Preparation of bile acid iron (II) salts

PREPARATION 10 g of acid are dissolved in 7.5 volumes of water with the minimum amount of sodium hydroxide (=10%, 20% for the emisuccinate), at pH 8.

When dissolution is complete, the mixture is added at 35° C., under stirring, with a $FeCl_3$ 6 $H_2O$ aqueous solution previously prepared dissolving 2.42 g (stoichiometric +10% excess to cholic or dehydrocholic acid), 2.53 g (stoichiometric +10% excess to deoxy cheno and ursodeoxy acids), or 5.02 g (stoichiometric +10% excess to emisuccinate) of ferric salt slowly dissolved in 25 ml of water.

The mixture is stirred to complete precipitation, then the precipitate is washed until chlorides disappear. Yield: above 95%.

In the following, the characteristics of the obtained salts are reported.

| Salt | M.p. | Iron content |
|---|---|---|
| Ferric cholate ferric (3α, 7α, 12α trihydroxide 5β-cholanate) | 237–239° C. | 4.07–4.67 |
| Ferric deoxycholate ferric (3α, 12α dihydroxy-5β-cholanate) | 218–219° C. | 4.24–4.84 |
| Ferric dehydroxycholate iron (3, 7, 12, 5β triketocholanate) | 216–218° C. | 4.13–4.73 |
| Ferric chenodeoxycholate ferric (3α, 7α-dihydroxy-5β-cholanate) | 214–218° C. | 4.24–4.84 |
| Ferric ursodeoxycholic ferric (3α, 7α-dihydroxy-5-β-cholanate) | 200° C. | 4.24–4.84 |
| Ferric hyodeoxycholate ferric (3α, 6α-dihydroxy-5-β | 193° C. | 4.24–4.84 |
| Disuccinyl ursodeoxycholate (ferric bio-emisuccinate 3α, 7α-dihydroxy-5β- cholanate) | 268–270° C. | 8.05–9.25 |

EXAMPLE 2

Figure 2:
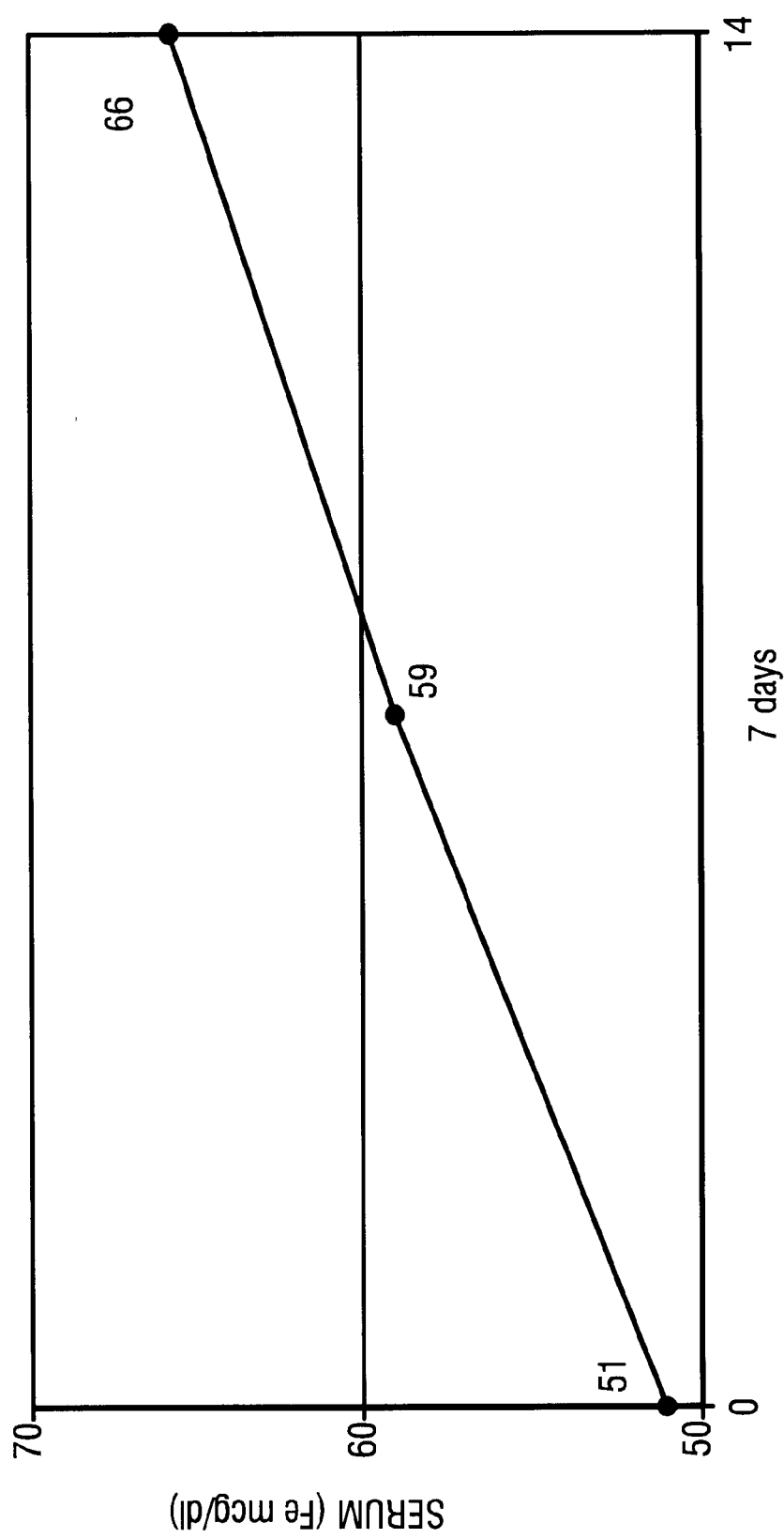
FIG. 2 is a graph of serum iron concentration (Fe mcg/dl) over a period fourteen days after administration of 19.2 mg iron per day in the form of ferric ursodeoxycholate to a second iron-deficient patient.

FIGS. 1 and 2 show the results of serum Fe obtained after administration of 19.2 mg Fe/day in the form of ferric ursodeoxycholate to two Fe-deficient patients.

What is claimed is:

1. The ferric salt of bis-hemisuccinyl-ursodeoxycholic acid.

2. A pharmaceutical or veterinary composition comprising an effective amount of the ferric salt of bis-hemisuccinyl-ursodeoxycholic acid.

3. A dietary supplement composition comprising the ferric salt of bis-hemisuccinyl-ursodeoxycholic acid in admixture with a carrier or excipient.

4. A method of treating iron deficiency in a patient comprising administering an effective amount of the ferric salt of bis-hemisuccinyl-ursodeoxycholic acid.

5. The method of claim 4 wherein the dose is from 100 mg to 3 grams one to four times daily.

6. A method of delivering metal cations selectively into the entero-hepatic circle of a human or of an animal comprising administering an effective amount of the ferric salt of bis-hemisuccinyl-ursodeoxycholic acid.

* * * * *